US00PP18409P3

(12) United States Plant Patent
Garrison et al.

(10) Patent No.: US PP18,409 P3
(45) Date of Patent: Jan. 8, 2008

(54) ***ASPARAGUS* PLANT NAMED 'NJ44P'**

(50) Latin Name: *Asparagus officinalis*
Varietal Denomination: NJ44P

(75) Inventors: Stephen A. Garrison, Pittsgrove, NJ (US); Chee-kok Chin, Holmdel, NJ (US); John J. Kinelski, Princeton, NJ (US)

(73) Assignee: Rutgers, The State University, New Brunswick, NJ (US)

( * ) Notice: Subject to any disclaimer, the term of this patent is extended or adjusted under 35 U.S.C. 154(b) by 0 days.

(21) Appl. No.: 11/431,187

(22) Filed: May 10, 2006

(65) Prior Publication Data

US 2007/0266465 P1 Nov. 15, 2007

(51) Int. Cl.
*A01H 5/00* (2006.01)

(52) U.S. Cl. ..... Plt./260

(58) Field of Classification Search ..... Plt./260
See application file for complete search history.

*Primary Examiner*—Kent Bell
*Assistant Examiner*—Annette H Para
(74) *Attorney, Agent, or Firm*—James A. Lucas; Driggs, Hogg & Fry Co., L.P.A.

(57) ABSTRACT

A female *asparagus* plant (*Asparagus officinalis*) denoted 'NJ44P' was developed through extensive culture and selection from a field of the variety Mary Washington. Plant 'NJ44P' has many desirable traits including vigorous plant growth, high yield, good resistance to rust (*Puccinia asparagi*) and good field tolerance to asparagus root rot (*Fusarium oxysporum*) and *asparagus* crown rot (*Fusarium mondiforme*). These desirable traits have been shown to be transmissible to its progenies. The invention relates to plants and plant parts of 'NJ44P' plant. The invention further relates to hybrid asparagus seeds and plants produced by crossing the *asparagus* 'NJ44P' plant with another *asparagus* plant.

1 Drawing Sheet

Latin name of the genus and species: The Latin name is *Asparagus officinalis*.

Variety denomination: The varietal denomination is 'NJ44P'.

CROSS REFERENCE TO RELATED APPLICATIONS

This application is related to the copending plant patent application Ser. No. 11/431,329 entitled HOMOZYGOUS MALE ASPARAGUS PLANT NJ 22-34, which is owned by the assignee of the present invention and is filed currently herewith.

BACKGROUND OF THE INVENTION

For an asparagus plant to be commercially viable and profitable, good yield is essential. It is well known that asparagus is susceptible to a number of diseases. Among the most devastating are rust caused by *Puccinia asparagi* d.c., (Kahn et al. 1952), crown rot caused by *Fusarium oxysporum* and root rot caused by *f. Proliferatum* (syn=f. Moniliforme) (Johnston et al., 1979; Guerrero et al., 1999). Of course, the presence of these diseases adversely impacts the yields and therefore the profitability of the product. Accordingly, resistance to these diseases is essential to commercial success.

BRIEF SUMMARY OF THE INVENTION

This invention relates to a new and distinct asparagus plant designated as 'NJ44P'. Plant 'NJ44P' possesses several desirable traits including vigorous growth habit, higher yield, resistance to rust (*Puccinia asparagi*), and good field tolerance to root and crown rot (*Fusarium oxysporum*) and (*Fusarium moniliforme*).

BRIEF DESCRIPTION OF THE DRAWINGS

The color notations have been selected from observations as compared with the Munsell Limit Color Cascade, Munsell Color. Colors are approximate as color depends on density of growth, horticultural practices, such as light level, fertilization rate, and other conditions and, therefore, the color characteristics of this new variety should be determined with reference to the observations described herein, rather than from this illustration alone. Furthermore, the coloration is not considered to be a distinguishing feature of this new variety.

DETAILED DESCRIPTION OF THE INVENTION

Figure 1:
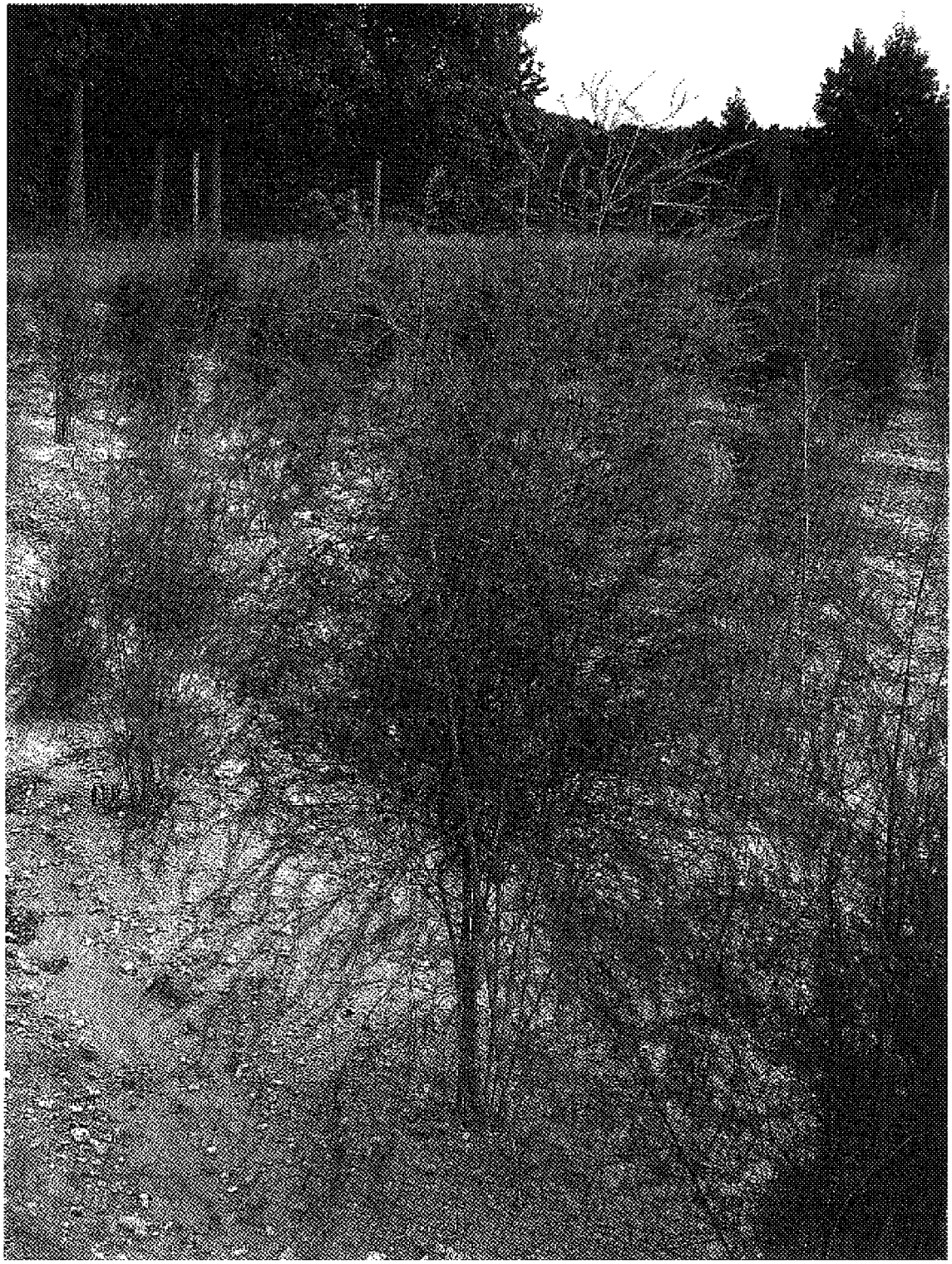
FIG. 1 shows the color as nearly representative as is possible to make the same, a typical plant of the new variety as it appears in a field under normal conditions.

An extensive program of asparagus plant development, carried out in a cultivated area in the vicinity of Bridgeton, and New Brunswick, N.J., has resulted in the development of a female *asparagus* plant 'NJ44P' with many desirable traits, which are transmissible to its progenies. 'NJ44P' was selected from a production field of "Mary Washington" asparagus located in southern New Jersey. The instant plant reproduces true to type in successive generations of asexual reproduction. Asexual reproduction was initiated via meristem culture and subsequently by clonal division in a laboratory in New Brunswick, New Jersey. The 'NJ44P' plant described herein was located at a trial field in Bridgeton, N.J. The data shown herein was collected when the plant was four years old.

Asparagus (*Asparagus officnalis* Linn.) is a dioecious species with individual plants being either male or female in sex. The 'cultivars' of asparagus today are morphologically similar but differ in local adaptation, yield, disease resistance, and longevity. Desirable cultivars are developed by crossing of elite male and female parents. Both male and female parents transmit traits such as disease resistance, yield, and spear morphology to their progenies. Disease resistance of the kind found in the 'NJ44P' plant and its progenies will allow growers to plant hybrids where rust and *Fusarium* now prevent profitable culture of susceptible varieties.

*Asparagus* can be clonally propagated by crown division. Crown is the structure where shoots and roots join together. Division or separation at the crown area will allow the propagation of asparagus. When propagated by crown division, successive generations of 'NJ44P' have similar morphological appearance and possess the same desirable characteristics as the original 'NJ44P' plant.

*Asparagus* can also be clonally propagated by tissue culture. An *asparagus* shoot tip or meristem when cultured on appropriate nutrient medium and appropriate conditions can grow, develop, and regenerate into a plant. Also, asparagus plant parts such as a spear segment when cultured on appropriate nutrient medium and appropriate conditions can grow, develop, and regenerate into an asparagus plant. Such plant can be efficiently divided and multiplied in appropriate nutrient medium. A 'NJ44P' plant propagated by such tissue culture has been found to retain the same desirable characteristics as the original 'NJ44P' plant.

When crossed with different male plants, asparagus 'NJ44P' can transmit many of its desirable traits including vigorous growth habit, higher yield, resistance to rust (*Puccinia asparagi*), and good field tolerance to root and crown rot (*Fusarium oxysporum*) and (*Fusarium moniliforme*) to its progenies.

The following table shows that in yield and disease resistance the progenies of 'NJ44P' compare very favorably to Jersey Giant (U.S. Plant Pat. No. 5,551) and Jersey Knight (U.S. Plant Pat. No. 6,624), two of most popular asparagus varieties in the world today.

TABLE 1

| | Jersey Giant | Jersey Knight | 'NJ44P' × 22-8 | 'NJ44P' × 22-34 |
|---|---|---|---|---|
| Yield, LB/Acre | 5160 | 4572 | 5200 | 4900 |
| Rust resistance | 4.7 | 6.8 | 5 | 6.4 |
| *Fusarium* tolerance | Tolerant | Tolerant | Tolerant | Tolerant |

Rust resistance: 0: no resistance, 10: complete resistance.

BOTANICAL DESCRIPTION

Data that distinguishes *asparagus* plant 'NJ44P' from other *asparagus* varieties that have been internally developed, as well as *asparagus* plants that are known and available commercially in the markets have been accumulated and are presented below.

The data (averages from 3 clones) are assembled in the following table: ASPARAGUS PLANT; 'NJ44P'.

TABLE 2

Stalk data:

Number of nodes below first branch: 28.67.
Distance from crown to first branch: 54.4 cm.
Color of stalk below first branch, bloom removed: Color No. 22-9.
Number of branches: 48.67.
Distance between first and last branch: 139.28 cm.
Color of stock between first and last branch, bloom removed: Color No. 21-13.
Internode length between branches: 2.86 cm.
Number of cladophyll nodes beyond last branch: 37.67.
Length beyond last branch: 28.15 cm.
Color of stock beyond last branch: Color number 20-12.
Largest stalk diameter: 18.67 mm.
Mean diameter of three largest stalks: 16.77 mm.
Number of stalks: 20.67.
Highest headed stalk: 222.25 cm.
Typical and observed branch color: Color Number 20-10.

Flower data:

All vegetative and reproduction arts glabrous and appearing non-glandular.
Bracts subtending inflorescence branches triangular, scale-like, membranous, especially towards margins, not keeled or winged, with small hanging appendix from dorsal midvein close to stem; margins entire; apex acute.
Tepals 6 in two whorls, forming campanulate corolla at anthesis, syntepalous for lowest 1 mm, free above, 3.5-3.8 mm long, 1.3-1.6 mm wide, dorsally slightly thickened, apex outer surface margin color 26-3, apex inner surface margin color 26-4, apex outer surface middle color 22-7, apex inner surface middle color 24-6; base outer surface color 26-10, base inner surface color 26-9; base outer surface middle color 22-11; base inner surface middle color 22-5; straight in bud, recurved apically at anthesis, margin entire, strongly membranous; apex bluntly acute to obtuse, often twisted or crinkled after anthesis due to drying out of membranous area.
Flower width at midpoint: 2.0 mm.
Typical number of flowers per cluster (flowering node): 2.

Fruit

Weight of 100 fruit (from 'NJ44P' × 22-8): 28.7 g.
Water displacement of 100 fruit: 33 mL.
Number of seeds per 100 fruit: 353.
Weight of seeds per 100 fruit: 8.4 g (30 days after harvest).
Water displacement of seed of 100 fruit: 11 mL.
Mature fruit Color: No. 33-12.3.
Cladophyll data:

Cladophyll

Average number per first node: 5.8
Shape: linear, filiform, needle-like; apex acute; base cunneate, margin—entire; Color—20-9.

Leaves

Main stem leaves scale-like, triangular, average 12 mm long, 9 mm wide at base, membranous: apex acuminate; base truncate; margin hyaline; Color—26-9 abaxial; 26-8 adaxial.
Terminal branch leaves scale-like, triangular, average 5 mm long, 3 mm wide at base, membranous: apex acuminate; base truncate; margin erose, hyaline. Color: 26-7 abaxial; 25-7 adaxial.

Reproductive Organs

Stamens—6 in number, rudimentary, free from tepals and each other, arranged in tepal sinuses and in dorsal position to innermost whorl of tepals
Filaments—filiform, slightly widened towards base, 0.9-1.0 mm long, 0.2-0.3 mm wide, about 0.3 mm wide at base.
Anthers sterile, without pollen, strongly flattened, sagittate to widely triangular, basifix about 0.6 mm long and about 0.3 mm wide at base.
Gynoecium—tricarpellate, with visible sutures along ovary and style
Ovary sessile, elliptic to obovate, 1.8-2.4 mm long, 1.3-1.6 mm wide at anthesis, color 21-11; plancentation axile; ovules 4-6 circular; style 1, fused from 3, filiform, sometimes curved, 1.2-1.4 mm long, color 24-6; Stigma 3, filiform, papillate on abaxial surface, spreading to horizontal level, 0.3 mm long, color 24-1.

What is claimed is:

1. A new and distinct variety of *Asparagus* Plant 'NJ44P' as herein shown and described.

* * * * *